(12) United States Patent
Boehringer et al.

(10) Patent No.: US 7,754,937 B2
(45) Date of Patent: Jul. 13, 2010

(54) WOUND PACKING MATERIAL FOR USE WITH SUCTION

(75) Inventors: John R. Boehringer, Wynnewood, PA (US); John Karpowicz, Chester Springs, PA (US); Amitabha Mitra, Voorhees, NJ (US); Christopher L. Radl, Malvern, PA (US)

(73) Assignee: Boehringer Technologies, L.P., Phoenixville, PA (US)

( * ) Notice: Subject to any disclaimer, the term of this patent is extended or adjusted under 35 U.S.C. 154(b) by 666 days.

(21) Appl. No.: 10/981,119

(22) Filed: Nov. 4, 2004

(65) Prior Publication Data

US 2005/0209574 A1 Sep. 22, 2005

Related U.S. Application Data

(60) Provisional application No. 60/554,158, filed on Mar. 18, 2004.

(51) Int. Cl.
 A61F 13/00 (2006.01)
 A61F 15/00 (2006.01)
 A61M 1/00 (2006.01)
(52) U.S. Cl. .................. 602/53; 602/41; 604/304; 604/313
(58) Field of Classification Search ............ 604/304, 604/543, 305, 313; 602/41, 53
 See application file for complete search history.

(56) References Cited

U.S. PATENT DOCUMENTS

| | | | |
|---|---|---|---|
| 3,703,897 A * | 11/1972 | Mack et al. | 602/43 |
| 4,138,460 A * | 2/1979 | Tigner | 264/159 |
| 4,685,914 A * | 8/1987 | Holtman | 604/368 |
| 5,034,006 A | 7/1991 | Hosoda et al. | |
| 5,100,396 A | 3/1992 | Zamierowski | |
| 5,176,663 A | 1/1993 | Svedman et al. | |
| 5,261,893 A | 11/1993 | Zamierowski | |
| 5,358,494 A | 10/1994 | Svedman | |
| 5,527,293 A | 6/1996 | Zamierowski | |
| 5,549,584 A | 8/1996 | Gross | |
| 5,636,643 A | 6/1997 | Argenta et al. | |
| 5,645,081 A | 7/1997 | Argenta et al. | |
| 5,939,339 A * | 8/1999 | Delmore et al. | 442/149 |

(Continued)

FOREIGN PATENT DOCUMENTS

EP 0619105 A1 10/1994

(Continued)

OTHER PUBLICATIONS

Svedman et al., A Dressing System Providing Fluid Supply and Suction Drainage Used for Continuous and Intermittent Irrigation, Annals of Plastic Surgery, Aug. 1986, vol. 17, No. 2, pp. 125-132.*

(Continued)

*Primary Examiner*—Melanie J Hand
(74) *Attorney, Agent, or Firm*—Caesar, Rivise, Bernstein, Cohen & Pokotilow, Ltd.

(57) ABSTRACT

A wound packing for use with suction is provided. The wound packing comprises a plurality of nonabsorbent synthetic polymeric fibers coupled together to form a nonabsorbent material suitable for placement in the wound of a mammal. A method for treating the wound in a mammal using the disclosed wound packing is also provided.

12 Claims, 15 Drawing Sheets

U.S. PATENT DOCUMENTS

| | | | |
|---|---|---|---|
| 6,071,267 | A | 6/2000 | Zamierowski |
| 6,126,701 | A | 10/2000 | Calogero |
| 6,345,623 | B1 | 2/2002 | Heaton et al. |
| 6,458,109 | B1 | 10/2002 | Henley et al. |
| 6,520,982 | B1 | 2/2003 | Boynton et al. |
| 6,582,810 | B2 * | 6/2003 | Heffelfinger ............. 428/297.4 |
| 6,695,823 | B1 | 2/2004 | Lina et al. |
| 6,767,334 | B1 | 7/2004 | Randolph |
| 6,800,074 | B2 | 10/2004 | Henley et al. |
| 6,885,135 | B2 | 4/2005 | Kanao et al. |
| 6,897,349 | B2 * | 5/2005 | Gibbins et al. ................. 602/48 |
| 2001/0031943 | A1 | 10/2001 | Urie |
| 2001/0043943 | A1 | 11/2001 | Coffey |
| 2002/0065494 | A1 | 5/2002 | Lockwood et al. |
| 2002/0082567 | A1 * | 6/2002 | Lockwood et al. .......... 604/307 |
| 2002/0115952 | A1 | 8/2002 | Johnson et al. |
| 2003/0093050 | A1 * | 5/2003 | Baker .......................... 604/378 |
| 2004/0002676 | A1 * | 1/2004 | Siegwart et al. ............... 602/58 |
| 2004/0006319 | A1 | 1/2004 | Lina et al. |
| 2004/0030304 | A1 | 2/2004 | Hunt et al. |
| 2004/0039415 | A1 | 2/2004 | Zamierowski |
| 2004/0054338 | A1 | 3/2004 | Bybordi et al. |
| 2004/0089412 | A1 * | 5/2004 | Topolkaraev ................ 156/250 |
| 2004/0093026 | A1 | 5/2004 | Weidenhagen et al. |
| 2004/0122434 | A1 | 6/2004 | Argenta et al. |
| 2004/0127862 | A1 | 7/2004 | Bubb et al. |
| 2004/0127863 | A1 | 7/2004 | Bubb et al. |

FOREIGN PATENT DOCUMENTS

| | | | |
|---|---|---|---|
| WO | WO 80/01139 | | 6/1980 |
| WO | WO 91/00718 | | 1/1991 |
| WO | WO 01/34079 | A1 | 5/2001 |
| WO | WO 03/057070 | A2 | 7/2003 |
| WO | WO 2004/037334 | A1 | 5/2004 |
| WO | WO 2005/046762 | A1 | 5/2005 |

OTHER PUBLICATIONS

Marois et al., Endothlial Cell Behavior on Vascular Prosthetic Grafts: Effect of Polymer Chemistry, Surface Structure, and Surface Treatment, ASAIO Journal 1999, pp. 272-280.*

Chariker et al., Effective management of incisional and cutaneous fistulae with closed suction wound drainage, Contempory Surgery, vol. 34, Jun. 1989, pp. 59-63.

Ko; Fabrics, Encyclopedia of Biomaterials and Biomedical Engineering, 2004, Draft Copy, pp. 1-38.

Ma, Scaffolds for tissue fabrication, Materialstoday, May 2004, pp. 30-40.

Saxena et al., Vacuum-Assisted Closure: Microdeformations of Wounds and Cell Proliferation, Plastic and Reconstructive Surgery, Oct. 2004, vol. 114, No. 5, pp. 1086-1096.

Schein et al., The 'sandwich technique' in the management of the open abdomen, Br. J. Surgery, May 1986, vol. 73., No. 5, pp. 369-370.

Williams, Benefit and risk in tissue engineering, Materialstoday, May 2004, pp. 24-29.

Svedman, et al., "Irrigation Treatment of Leg Ulcers", *The Lancet*, Sep. 1983, pp. 531-534.

Svedman, et al., "Irrigation Treatment in Split-Thickness Skin Grafting of Intractable Leg Ulcers", *Scandinavian Journal of Plastic and Reconstructive Surgery*, 1985; vol. 19; pp. 211-213.

* cited by examiner

WOUND PACKING MATERIAL FOR USE WITH SUCTION

CROSS REFERENCE TO RELATED APPLICATIONS

This application claims the benefit of priority to U.S. Provisional Patent Application No. 60/554,158, filed on Mar. 18, 2004, the contents of which are incorporated in this application by reference.

FIELD OF THE INVENTION

The invention relates to a device and method for treating wounds. More specifically, the present invention relates to a therapeutic wound packing material for use with suction and a method of treatment employing the same.

BACKGROUND OF THE INVENTION

Large open chronic wounds typically secrete exudates during the healing process. It is generally desirable to remove these wound exudates from the wound vicinity to minimize bacterial growth which can cause infection and delay healing. Excessive exposure to wound exudates can result in maceration of the skin surrounding the wound. Wound exudates are known to contain tissue degrading enzymes that can impede wound healing. It is generally known to cope with exudates of large open chronic wounds by packing them with an absorbent packing such as gauze. Gauze packing fills dead space in the wound and absorbs exudates released by the tissue over time. Disadvantageously, the absorbent gauze must be replaced periodically as it absorbs a larger volume of exudates and becomes saturated.

Alternatively, removal of wound exudates can be accomplished with suction. The wound is sealed generally by the application of a cover and suction is applied to the wound to draw out exudates. Often the suction is applied continuously for days or weeks. When suction is used it can be beneficial to also use wound packing. The wound packing provides passages from the areas where it contacts the wound to communicate the exudates from the wound surface towards the source of suction. When wound packing is used in conjunction with suction it is generally found that wounds heal more quickly and wound packing may be replaced less frequently because exudates are continuously removed.

When absorbent wound packings such as gauze are used with suction their highly absorbent characteristics are not required. Cotton gauze typically absorbs from ten to twenty five times its weight in aqueous liquid. This absorbent quality can be detrimental because absorbent packings tend to retain volumes of exudates within the wound cavity and adjacent the wound surface supporting bacterial growth and enzymatic breakdown of tissue.

When suction has been applied to the wound, it is generally desirable to permit the wound to contract. Wound contraction is a normal part of wound healing, therefore using a packing that encourages contraction, as opposed to inhibiting it, is desirable. When a noncompressible wound packing, such as gauze, is used in conjunction with suction, the wound contraction may be impeded by the wound packing.

An alternative to gauze as a wound packing is foam. Foams have the disadvantage that they are not readily modified by many traditional methods, such as heat stamping, to produce a surface texture after they are formed. Foam formation methods do not readily lend themselves to the construction of composites. This limits the extent to which multiple materials can be integrated into the foam structure during the manufacturing process. Foam materials are isotropic in that they exhibit uniform properties such as absorbency, pore size etc. in all directions. When used with suction foams, have the disadvantage that pieces can easily be separated from the whole, when removed from the wound. This is caused by new tissue growing into the foam structure. This can be problematic because often it may not be possible to see the pieces of foam that remain in the wound.

Hence, known wound packing materials have a number of disadvantages and as such there is a need for a superior wound packing.

SUMMARY OF THE INVENTION

To overcome the deficiencies of conventional wound treatment techniques and devices, the present invention is a wound packing material, a method for making the wound packing material, and a method of treating a wound employing the wound packing material.

According to an exemplary embodiment of the present invention, a wound packing for stimulating the healing of a wound in a mammal is provided. The exemplary wound packing comprises a plurality of polymeric nonabsorbent fibers coupled together to form a nonabsorbent material suitable for placement within a wound of a mammal.

A further embodiment of the present invention is an anisotropic packing. Another embodiment of the wound packing has loft.

Yet a further embodiment of the wound packing is batting. An additional embodiment of the wound packing is resilient.

An alternative embodiment of the wound packing includes a wound healing substance incorporated into the component fibers and/or coated onto the component fibers.

According to a yet further embodiment of the present invention, a wound packing for stimulating the healing of a wound is provided comprising a plurality of polymeric nonabsorbent fibers randomly coupled together to form a sheet of nonabsorbent material suitable for placement within a wound of a mammal.

Further aspects of the sheet embodiment of the present invention are provided that comprise a corrugated three-dimensional structure and methods of manufacturing the same.

According to another aspect of the present invention, a method is provided for treating a wound of a mammal comprising the steps of placing a fibrous nonabsorbent wound packing material in contact with at least one surface of a wound and applying suction to the wound and wound packing material.

These and other aspects will become apparent from the following description.

BRIEF DESCRIPTION OF THE DRAWINGS

The invention is best understood from the following detailed description when read in connection with the accompanying drawing. It is emphasized that, according to common practice, the various features of the drawing are not to scale. On the contrary, the dimensions of the various features are arbitrarily expanded or reduced for clarity. Included in the drawing are the following Figures.

DETAILED DESCRIPTION OF THE INVENTION

Figure 1:
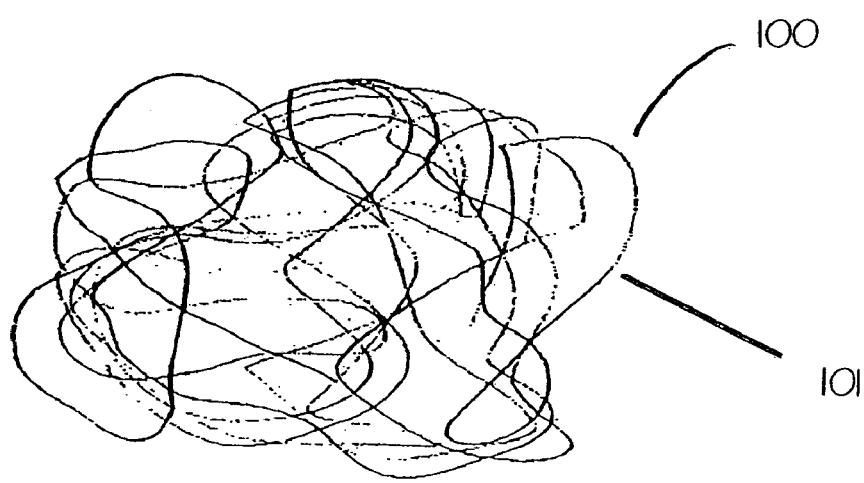
FIG. 1 is an illustration of an exemplary embodiment of a wound packing material of the present invention.

Nonabsorbent wound packing has an advantage because it communicates exudates away from the wound and toward a source of suction more quickly and more completely. A component nonabsorbent fiber material, for the purposes of wound packing, is one that absorbs less than about 20% its weight in aqueous liquid. However, absorbency of a wound packing material is more appropriately characterized as volume of liquid absorbed by volume of packing (in its uncompressed state). Thus, a nonabsorbent wound packing preferably retains less than about one third its volume in aqueous liquid. More preferably, it retains less than about 11% its volume. Most preferably, it retains less than about 5% its volume. The absorbency of a wound packing is a function of a number of physical properties. Among them are density, wettability of the base material, the extent to which the base material swells with absorption, surface characteristics of the individual fibers (if any), and the geometric organization of the base material that forms the wound packing.

Compressibility is a measure of a material's ability to reduce its volume under compression. A compressible wound packing permits wound contraction under suction. Generally the wound and wound packing are sealed with a flexible cover. A suction is then applied beneath the cover creating a pressure below atmospheric pressure. The pressure differential between atmospheric pressure and the pressure at the wound packing creates a compressive force on the wound packing. A compressible wound packing also adapts to changes in wound geometry induced by patient movement and wound contraction so that it continues to conform to wound geometry. The compressibility of a wound packing is a function of a number of physical characteristics. Chief among these characteristics is the proportion of void volume. A high void volume permits the wound packing to deform in response to a compression force.

While it is generally advantageous to permit a wound to contract under suction, it is often preferable to encourage the wound to contract in one direction in favor of a second and/or third direction. A material whose response to a compressive force varies depending upon the direction from which the force is received is described as anisotropic. In a wound care application, it may, for example, be preferred to promote contraction of a wound's "width" while maintaining the wound's length as well as the wound's depth. Alternatively, it may be desirable to maintain the relative position of the wound's margins while encouraging healing from the wound bed.

Another desirable characteristic of a wound packing is resiliency. A resilient material resumes its shape and volume after exposure to compression. A resilient wound packing expands to fill a wound. This is an advantageous feature because the wound packing should contact all surfaces of a wound so that wound exudates can be drawn away from all wound surfaces by suction. Dead spaces within a wound where no packing is present can fill with wound exudates that impede wound healing. Further, a resilient wound packing will discourage overpacking in a clinical setting because it expands once it is packed into a cavity wound. A resilient packing also has a beneficial ability to resume its configuration when suction is stopped and resumed or after a patient moves. This is also important when suction is applied to the wound in an intermittent fashion.

It is also generally desirable to use wound packing that will maintain its integrity such that it does not easily break apart or degrade and subsequently leave material in a wound. Materials that demonstrate this quality can be described as "non shedding." Non shedding materials also have the advantage of being able to be purposely cut to fit an irregular wound without breaking apart. Materials with a high degree of integrity are advantageous in that pieces of such materials are much less likely to break away from the whole and get lodged in the wound bed.

FIG. 1 illustrates an exemplary embodiment of the present invention. As shown in FIG. 1, wound packing 100 is a mass of fibers 101 randomly coupled together. The fibrous mass can take the form of a simple batting material having a desirable loft. Alternatively, this batting can be constructed from a single tangled monofilament material. Wound packing 100 is resilient and compressible so that it can easily conform to an irregular wound. Preferably, wound packing 100 is nonwoven. More preferably, wound packing 100 is spunbonded or melt blown. Component fibers 101 are comprised of a nonabsorbent synthetic polymer. Examples of suitable biocompatible materials are polyolefins such as polypropylene and polyethylene, polyamides such as nylon and related aramids, and polyester. Additionally, fiber treatments such as hyaluronic acid or antimicrobial silver may be incorporated into wound packing 100. Component fibers with one or more of the following beneficial properties are anticipated. Fibers can be bio-absorbable, they may be bio-erodable for the controlled release of a curative agent, they may be adherent for the selective removal of undesirable tissues, substances or microorganisms or they may be non-adherent for the protection of delicate tissue. More preferably, the fibers further incorporate one or more agents recognized in the art to promote wound healing. For example, calcium alginate fibers can be incorporated into wound packing 100. An embodiment is also contemplated wherein one or more of the fibers incorporated into wound packing 100 are sufficiently conductive to transmit a therapeutic current to the wound tissue from a suitable source (not shown).

Because it is composed of nonabsorbent fibers, wound packing 100 is itself substantially nonabsorbent. Non-absorbency is desirable to minimize retention of wound exudates within the wound packing 100. The minimized retention has the benefits of reducing wound exposure to the exudates (and attendant infection) and lessening the frequency with which the wound packing 100 must be changed. Wound packing 100 may have some apparent absorbency due to minor liquid retention via entrapment in the fibrous matrix and fiber surface adsorption. Alternatively, a controlled proportion of absorbency can be designed into the packing material 100 to permit a patient care provider to administer a medicated solution to the wound area over time by soaking the packing material 100 in the medicated solution.

Figure 2:
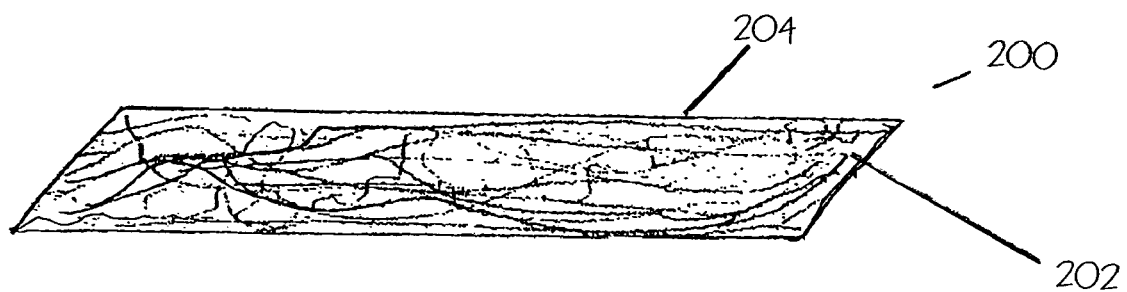
FIG. 2 is a perspective view of an exemplary wound packing sheet of the present invention.
Figure 5A:
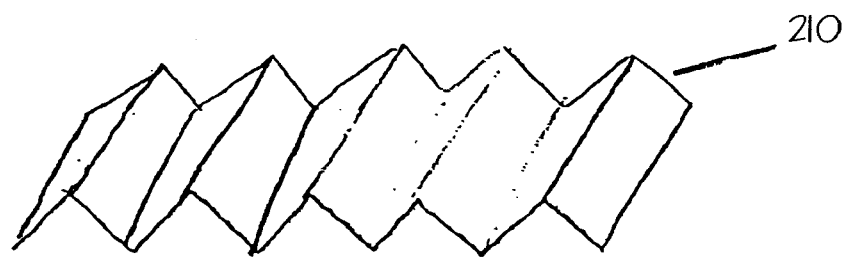
FIG. 5A is a perspective view of an exemplary pleated wound packing sheet of the present invention.
Figure 5B:
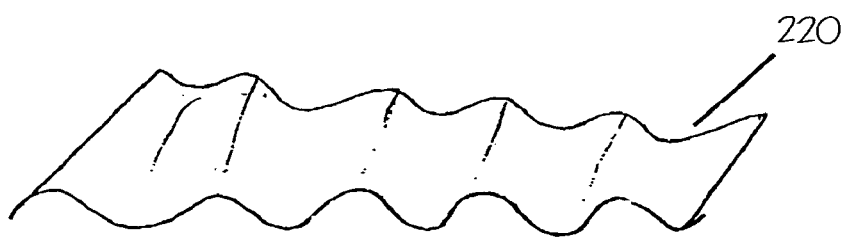
FIG. 5B is a perspective view of an exemplary contoured wound packing sheet of the present invention.
Figure 5C:
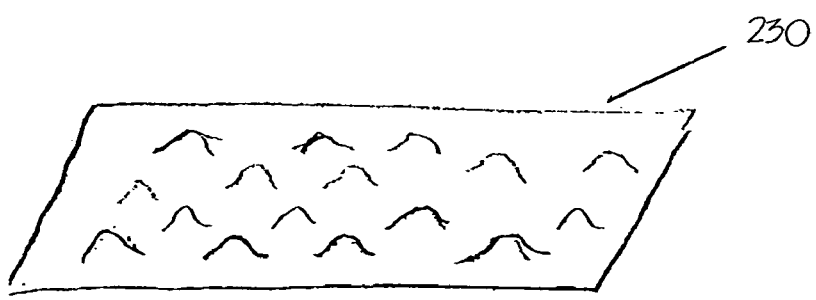
FIG. 5C is a perspective view of an exemplary embossed wound packing sheet of the present invention.
Figure 5D:
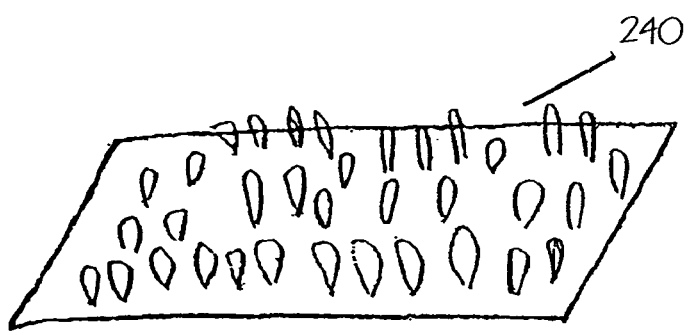
FIG. 5D is a perspective view of an exemplary looped wound packing sheet of the present invention.
Figure 5E:
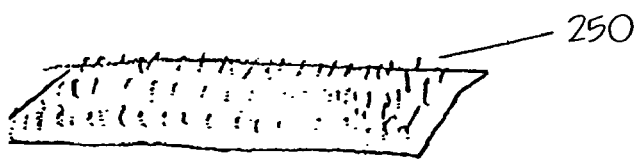
FIG. 5E is a perspective view of an exemplary velvet wound packing sheet of the present invention.

FIG. 2 illustrates another exemplary embodiment of the present invention. As shown in FIG. 2, wound packing sheet 200 comprises a plurality of nonabsorbent synthetic polymeric fibers 202 randomly coupled together to form a substantially flat sheet 204. Techniques are known in the textile arts that produce random fibrous materials and include, for example, carding, spunbonding and melt blowing. An example of a suitable material is the spunbond polypropylene Typar® manufactured by BBA Fiberweb™ Reemay, Inc. of Nashville, Tenn. Spunbond polypropylene is beneficial in that it facilitates the transport of liquids quite effectively. While wound packing sheet 200 is shown as being substantially flat it is recognized that it can be further manipulated by means known in the textile arts to provide substantial thickness. Potential structures are shown in FIG. 5A as a pleated sheet 210, FIG. 5B as a contoured sheet 220, and FIG. 5C as an embossed sheet 230. Further known steps would yield the fabrics with pile depicted in FIG. 5D and FIG. 5E, as a looped fabric 240 and a velvet fabric 250, respectively. Alternately tufting, as in carpet manufacturing may be utilized to produce a fabric with pile.

Figure 3A:
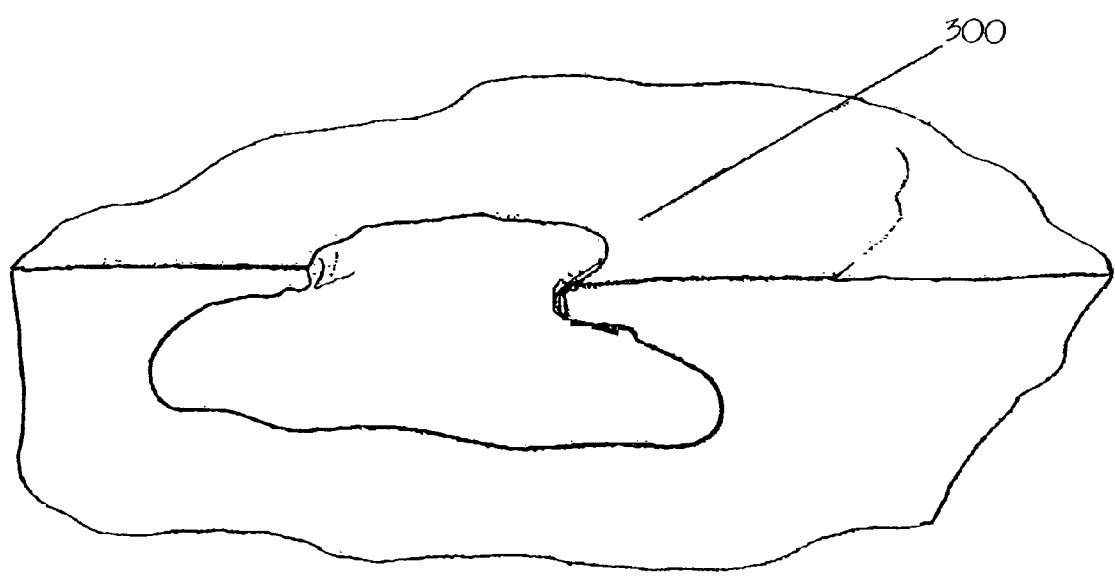
FIG. 3A is a cross sectional view of a deep tissue wound.
Figure 3B:
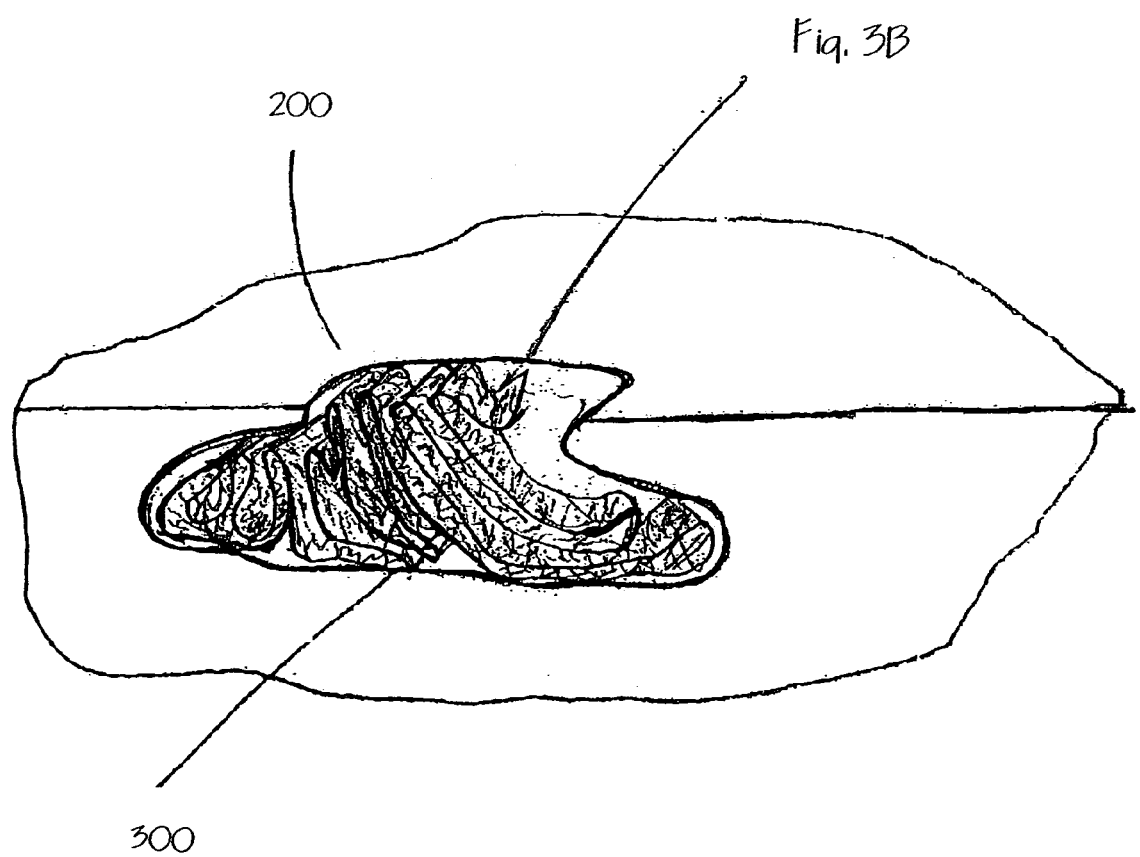
FIG. 3B is a cross sectional view of the deep tissue wound of FIG. 3A illustrated in combination with an exemplary embodiment of the present invention.

An exemplary deep tissue wound is illustrated in FIG. 3A. It comprises a wound cavity 300 suitable for treatment with wound packing in conjunction with suction. A wound packing is placed into the wound cavity 300. For example, FIG. 3B depicts wound packing sheet 200 packed into a wound cavity 300.

Figure 4:
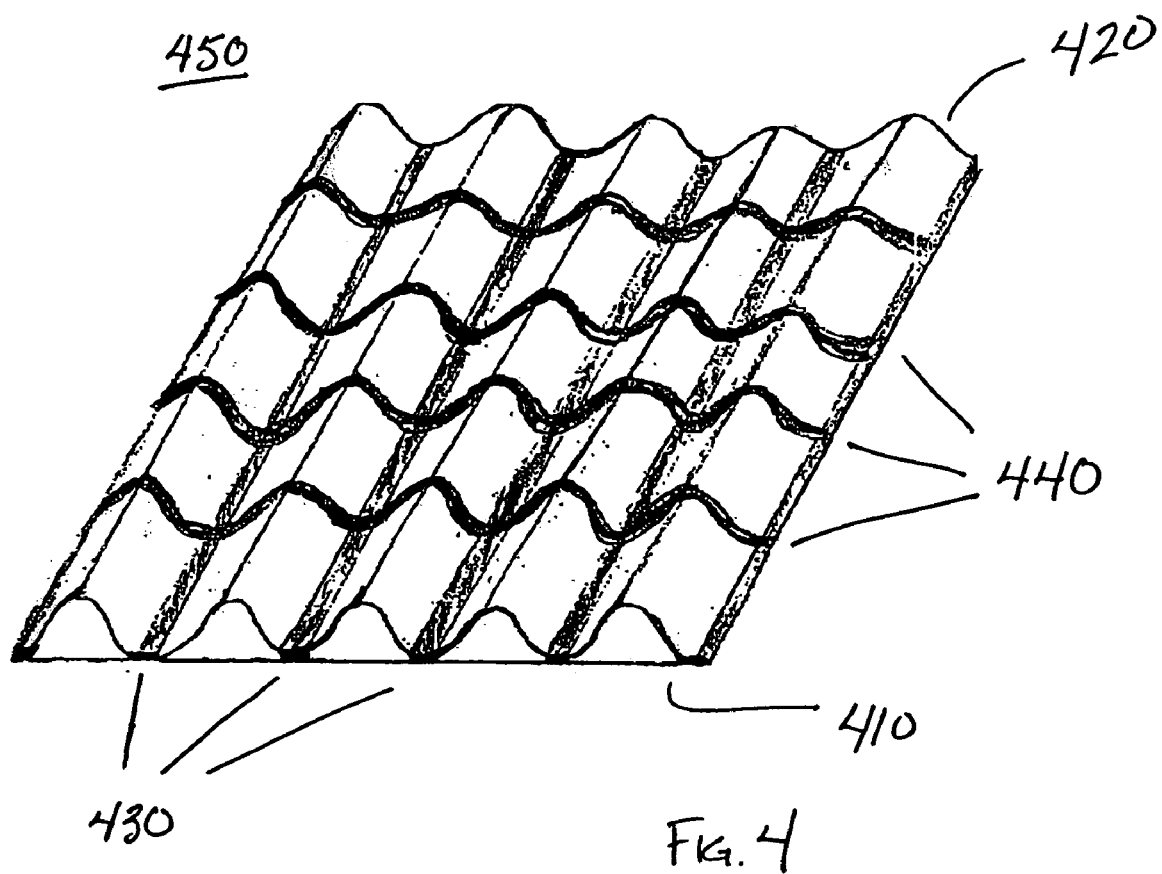
FIG. 4 is a perspective view of an exemplary corrugated unit of the present wound packing invention.

FIG. 4 illustrates an exemplary corrugated unit embodiment 450 of the present invention comprising two sheets. A first sheet layer 410 is provided, and a second sheet-like layer 420 having an essentially sinusoidal cross section, for example, is coupled to the surface of the first sheet layer at locations 430. The coupling can be achieved by use of an adhesive or heat sealing. A two part silicone adhesive has been found suitable to provide coupling between sheet 410 and sheet 420. A bead of silicone material 440 may be optionally added to adjust the resiliency of the corrugated unit 450. A suitable sheet material is Hollytex® spunbonded polyester manufactured by Ahistrom Corp. of Mt. Holly Springs, Pa. Hollytex® is a preferable choice because it is not prone to fiber shedding. Polyester fibers are preferred for this sheet because they absorb almost no fluid, transport liquids effectively, and are creep resistant in that they more readily return to their original configuration after having a force applied to them for a period of time. While it is preferable to make a corrugated unit embodiment from spunbond sheets, other base sheets are suitable as well. Such sheets may also be made from other nonwoven processes such as meltblowing or hydroentangling or from regular processes such as knitting or weaving. Although sheet layer 420 is illustrated as having a sinusoidal cross-section, the invention is not so limited. It is also contemplated that other cross-sections, such as pleated, may be used.

Figure 6A:
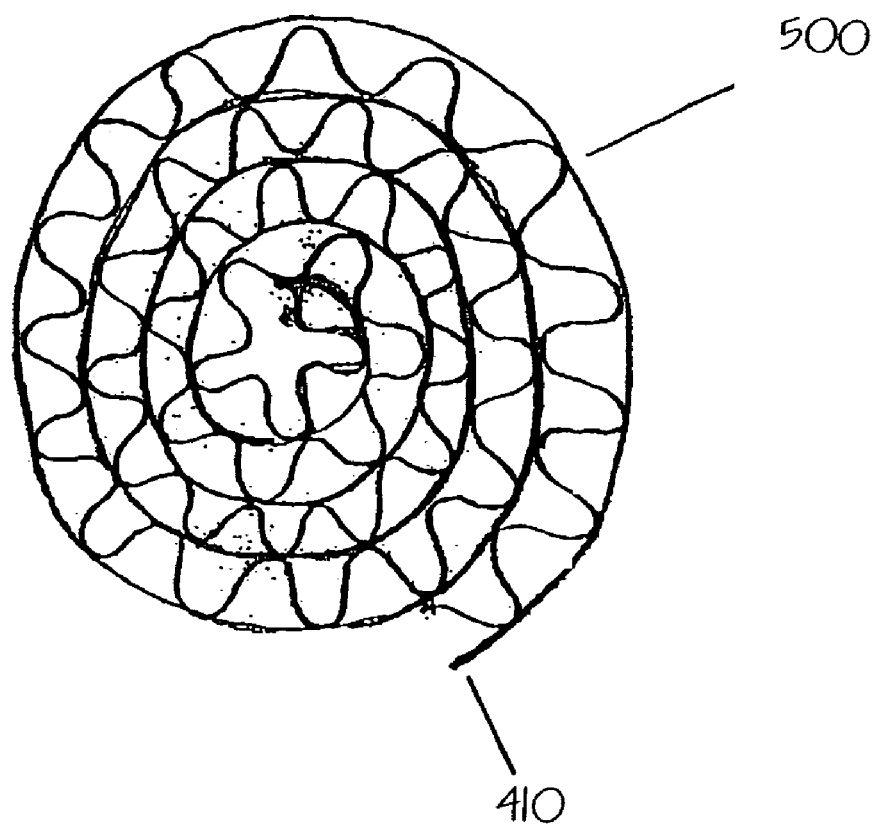
FIG. 6A is a top view of an exemplary spiral corrugated wound packing sheet of the present invention.
Figure 6B:
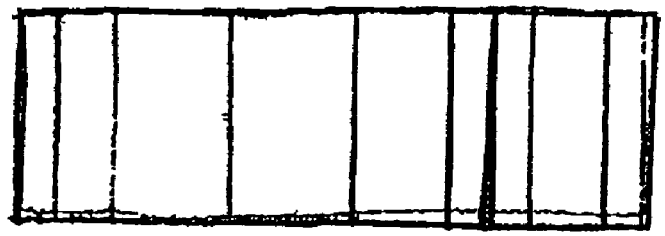
FIG. 6B is a side view of an exemplary spiral corrugated wound packing of the present invention.
Figure 7:
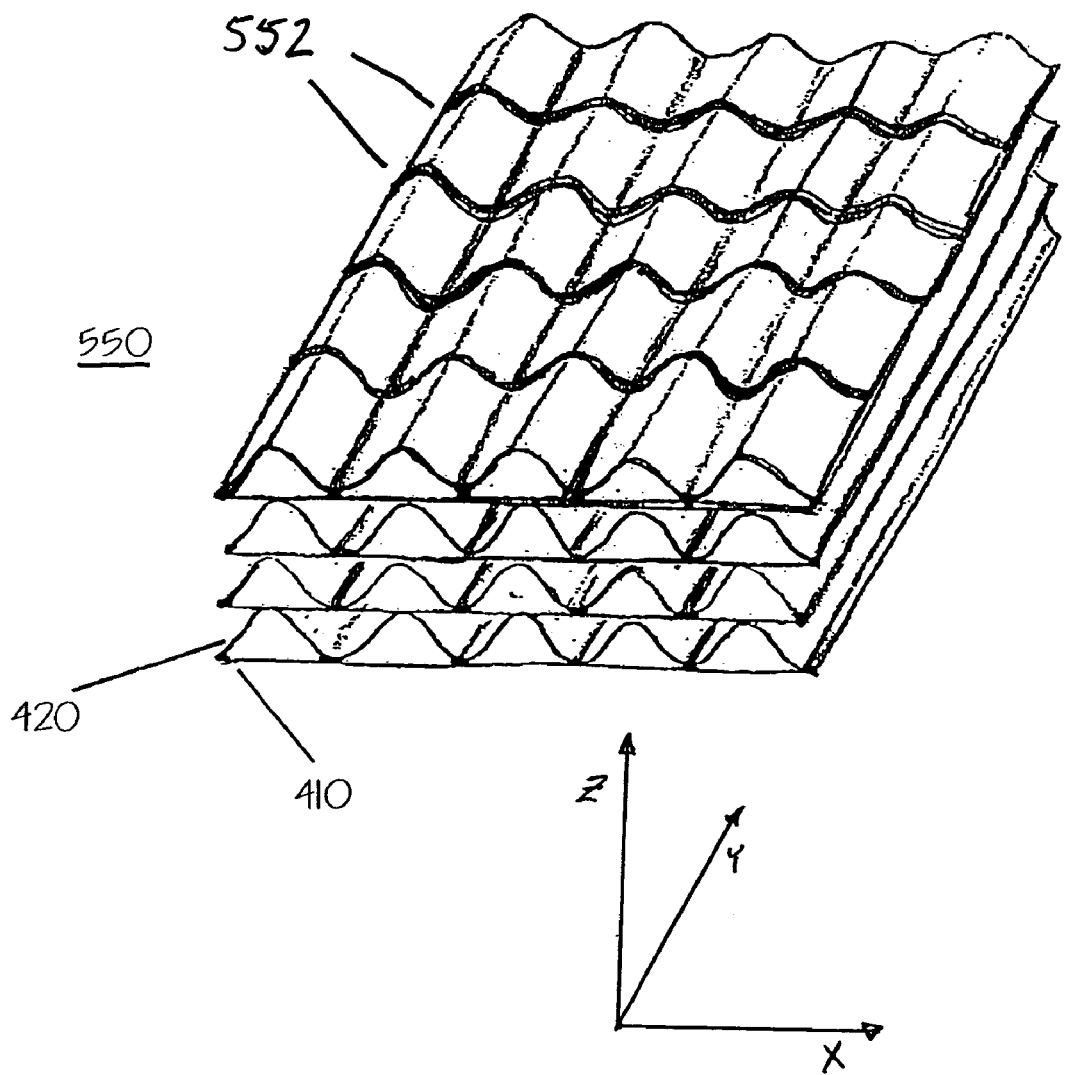
FIG. 7 is a perspective view of an exemplary multi-corrugated wound packing of the present wound packing invention.

Corrugated unit 450 can be used as a wound packing without further modification. It can also be used to form more complex three-dimensional structures. Spiral wound packing 500 illustrated in FIGS. 6A and 6B is formed by rolling corrugated unit 450 to expose a portion of the first flat sheet 410 along the circumference. More elaborate structures can also be formed from a plurality of corrugated units. For example, individual corrugated units may be coupled to each other by adhesive or heat sealing means to form multi-corrugated wound packing 550. One or more beads of silicone material 552 can serve dual purposes of coupling the corrugated units 450, as shown in FIG. 7, and improving the resiliency of the structure. It should be noted that, while FIG. 7 illustrates this embodiment with the peaks of each adjacent corrugation unit in alignment, a staggered configuration is also contemplated. Multi-corrugated wound packing 550 can also be sliced along a cross section at a suitable thickness to produce cut corrugated wound packing. Alternatively, wound packing 550 can be sliced at a bias to produce biased-cut corrugated wound packing.

Spiral wound packing 500, cut corrugated wound packing, and biased-cut corrugated wound packing have the benefit of being highly compressible and highly resilient. Preferably, these wound packing structures are sufficiently compressible to reduce to less than 50% of their original volume when subjected to the approximately 2 psi (pounds per square inch) compression force commonly encountered with the application of suction. More preferably, the wound packing is sufficiently compressible to reduce to less than 25% of its original volume. Most preferably, the wound packing is sufficiently compressible to reduce to less than 10% of its original volume.

It is desirable for these wound packing structures to be sufficiently resilient to resume more than 50% of their original volume after exposure to compressive forces common in a clinical setting. Such forces can be as high as 20 psi but are more routinely on the order of 1-2 psi. More preferably, these wound packing structures are sufficiently resilient to resume more than 80% of their original volume.

The structure of spiral wound packing 500, cut corrugated wound packing, and biased-cut corrugated wound packing may also be varied to more easily compress along one axis than the remaining two. This may be achieved by varying the angles at which the corrugated materials are cut or varying the amount and orientation of the adhesive used during manufacture of the corrugated unit. In particular, varying the amount and orientation of silicone adhesive beading has been found to enhance resiliency as well as control or enhance compressibility in a desired direction. For example, multi-corrugated wound packing 550 is generally anisotropic, having a different composite modulus of elasticity for each axis. This results in a packing that compresses preferentially in certain axes when vacuum is applied. This attribute is valuable when it is desirable to encourage the wound to close preferentially in one direction over another.

Figure 14A:
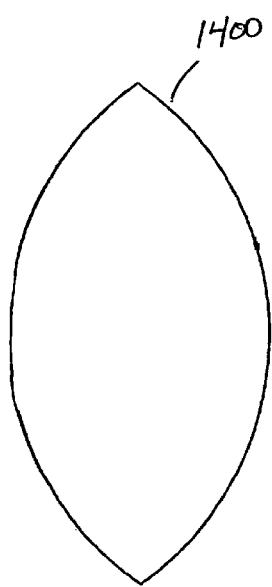
FIG. 14A is an illustration representing a wound.
Figure 14B:
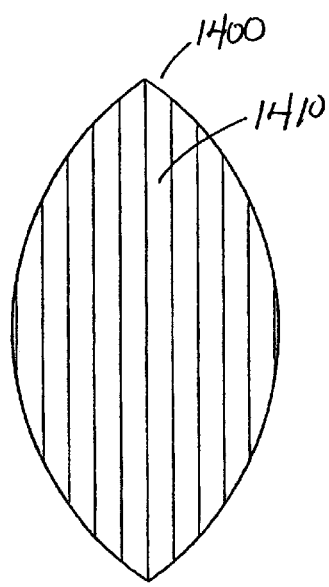
FIG. 14B is an illustration representing the wound of FIG. 14A with a wound packing of the present invention inserted into the wound.
Figure 14C:
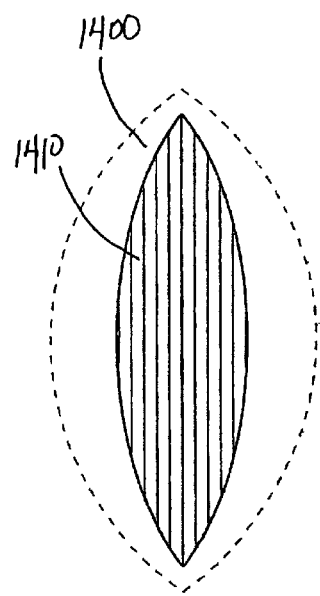
FIG. 14C is an illustration of the packed wound of FIG. 14C after suction is applied to the wound.

One version of multi-corrugated wound packing 550 has a modulus of elasticity of 0.9 psi in the x axis, 3.7 psi in the y axis, and 1.0 psi in the z axis. By way of example, if a 1" cube is cut out of multi-corrugated wound packing 550 and a 0.5 lb force is applied along each axis, the amount of compression in each direction is as follows; x axis—0.55 inches, y axis—0.16 inches and z axis—0.5 inches. FIG. 14A illustrates a wound 1400 that would benefit from an anisotropic wound packing 1410. FIG. 14B illustrates wound 1400 with an anisotropic packing 1410 prior to application of suction and FIG. 14C illustrates the wound with a contracted perimeter during application of suction with anisotropic packing 1410 in a compressed state. While specific composite moduli of elasticity are listed for 550, it will be clear to one skilled in the art that the moduli of elasticity of each axis of a packing material can be varied to suit a particular need.

Figure 8:
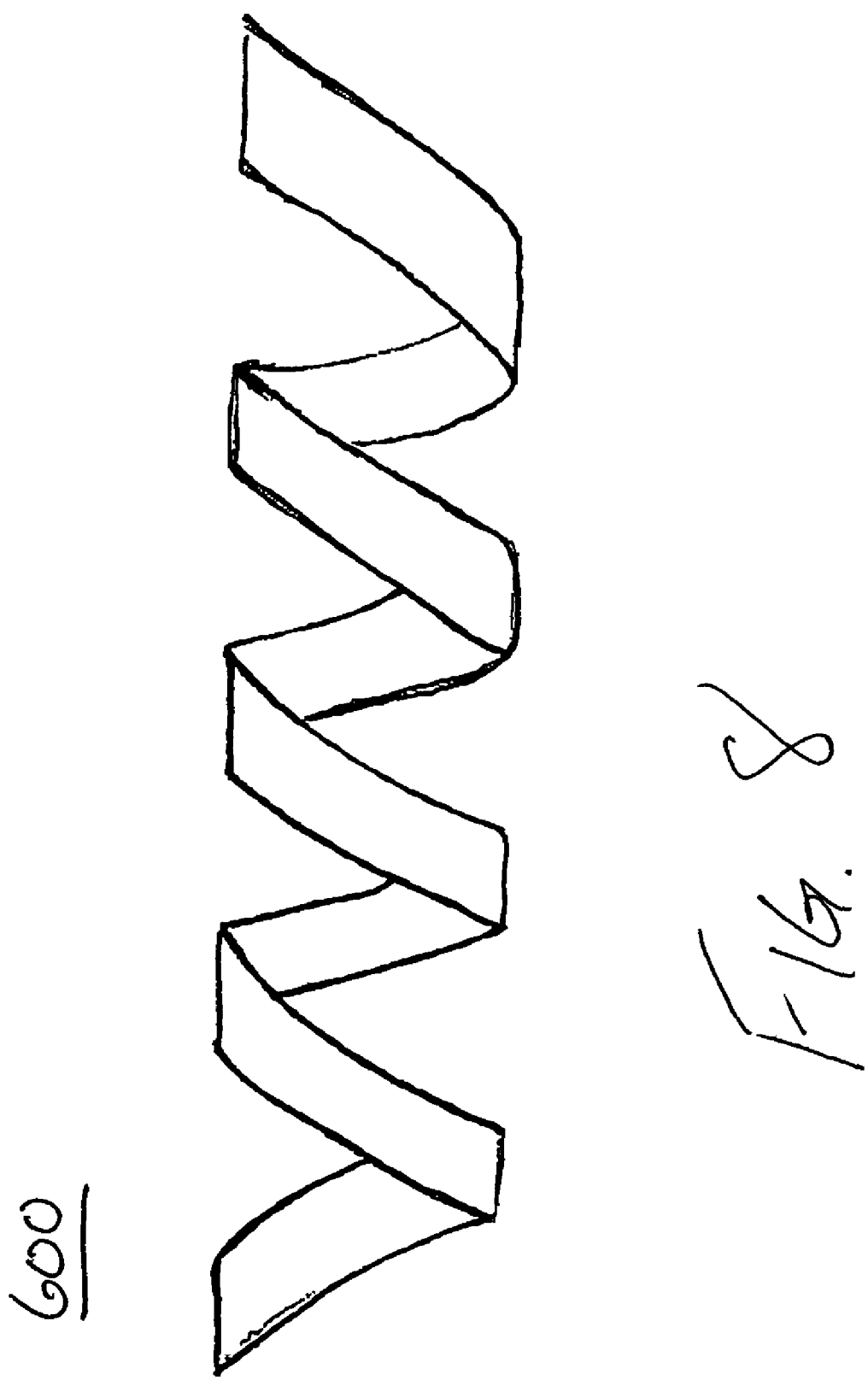
FIG. 8 is a perspective drawing of an exemplary corkscrew wound packing of the present invention.

FIG. 8 illustrates an exemplary corkscrew wound packing 600 of the present invention. The corkscrew wound packing can be formed simply by winding a single continuous sheet if desired. The spiraling structure of corkscrew wound packing 600 provides a substantially three dimensional structure with minimal manufacturing complexity. The spiraling corkscrew structure may be used as a packing as is or it can be configured with additional spiraling corkscrew structures to make a more elaborate three dimensional packing.

Figure 9:
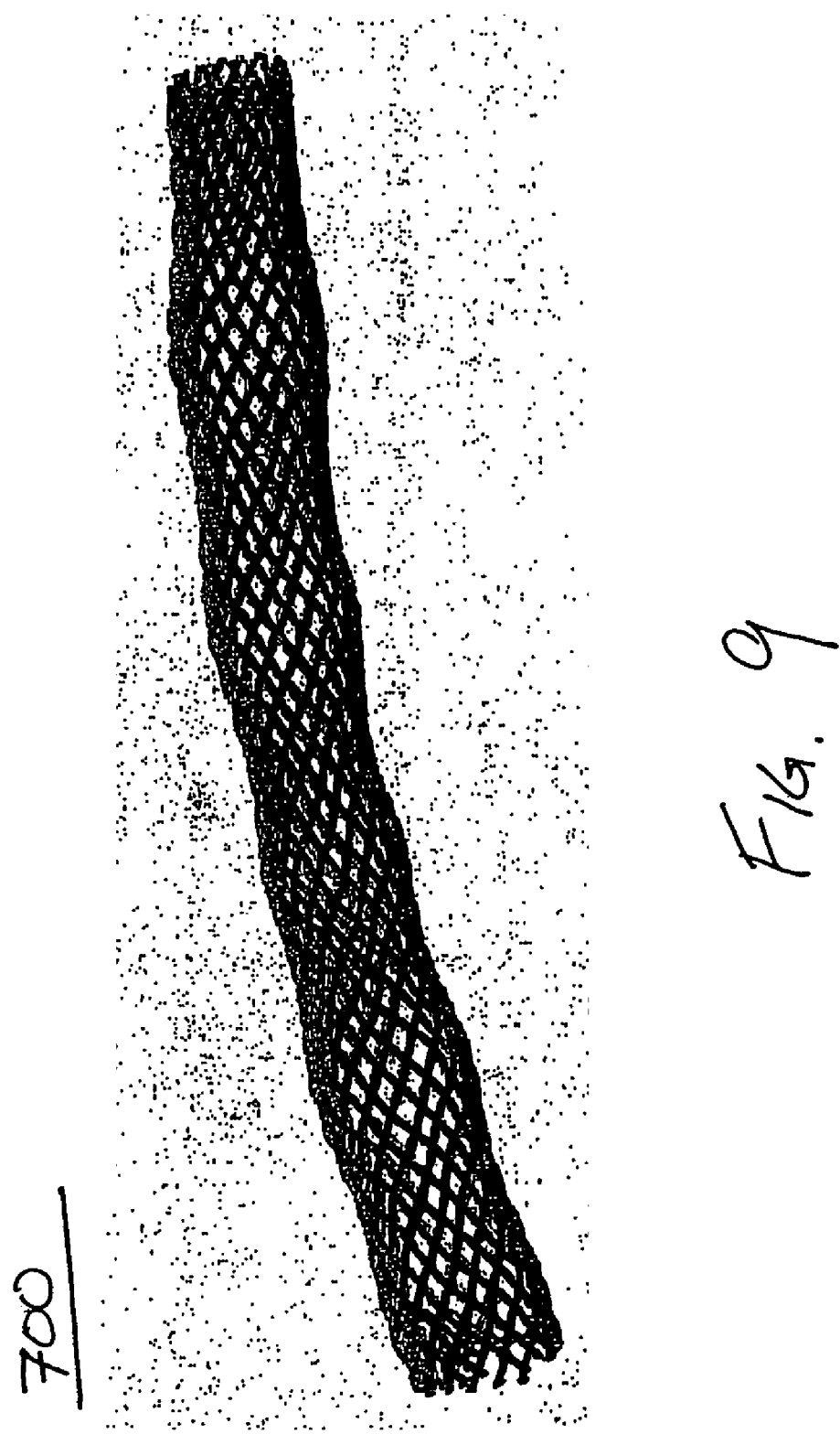
FIG. 9 is a perspective drawing of an exemplary hollow tube wound packing of the present invention.

FIG. 9 illustrates an exemplary hollow tubular wound packing 700 of the present invention. Tubular structure 700 can be formed by a variety of means known in the textile arts. In particular, it can be formed by braiding component fibers directly into the desired structure.

Figure 10:
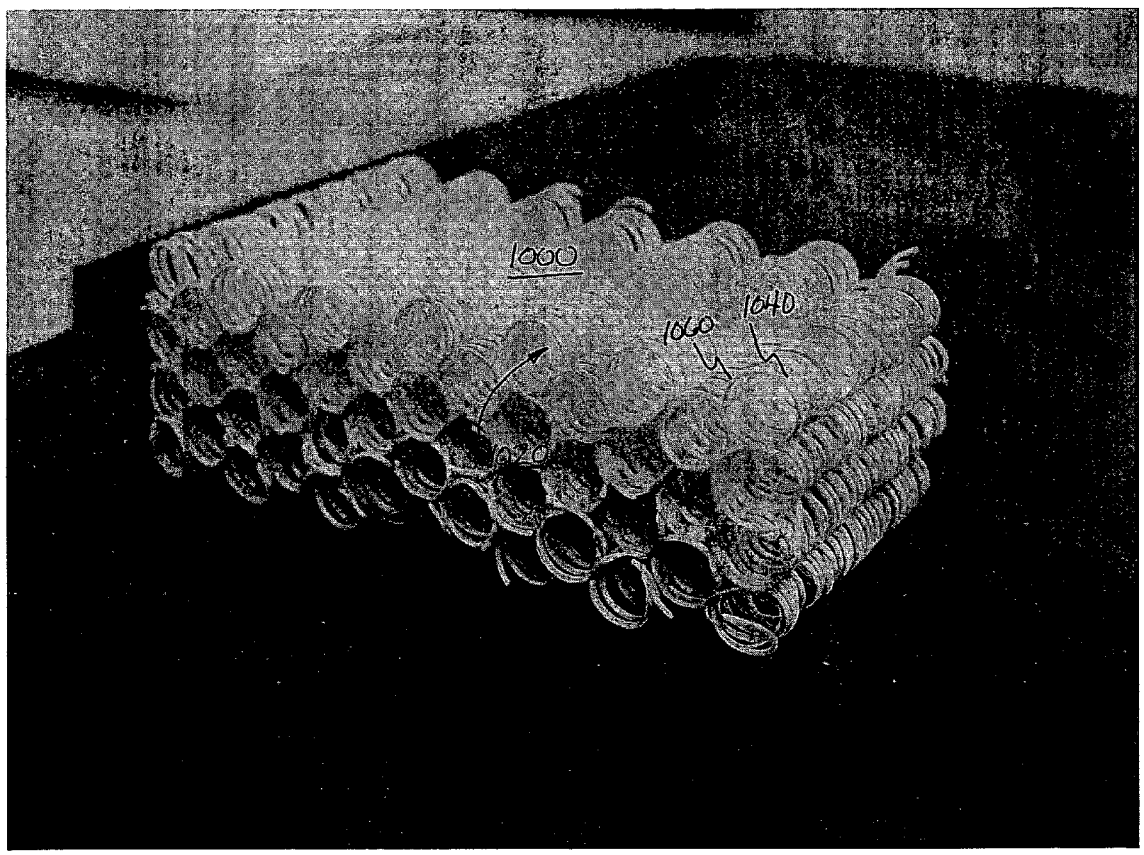
FIG. 10 is a picture illustrating an exemplary embodiment of a wound packing material of the present invention.
Figure 11:
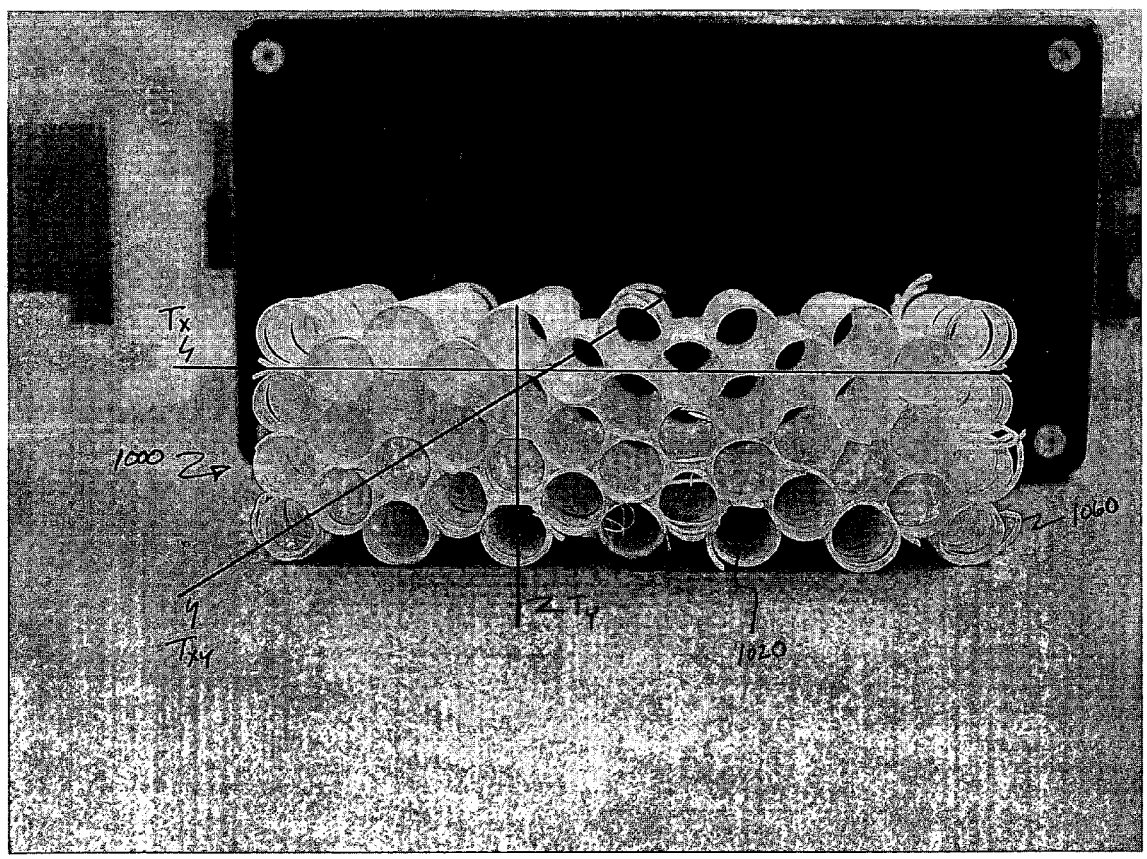
FIG. 11 is a picture illustrating a front view of the exemplary embodiment of FIG. 10.
Figure 12:
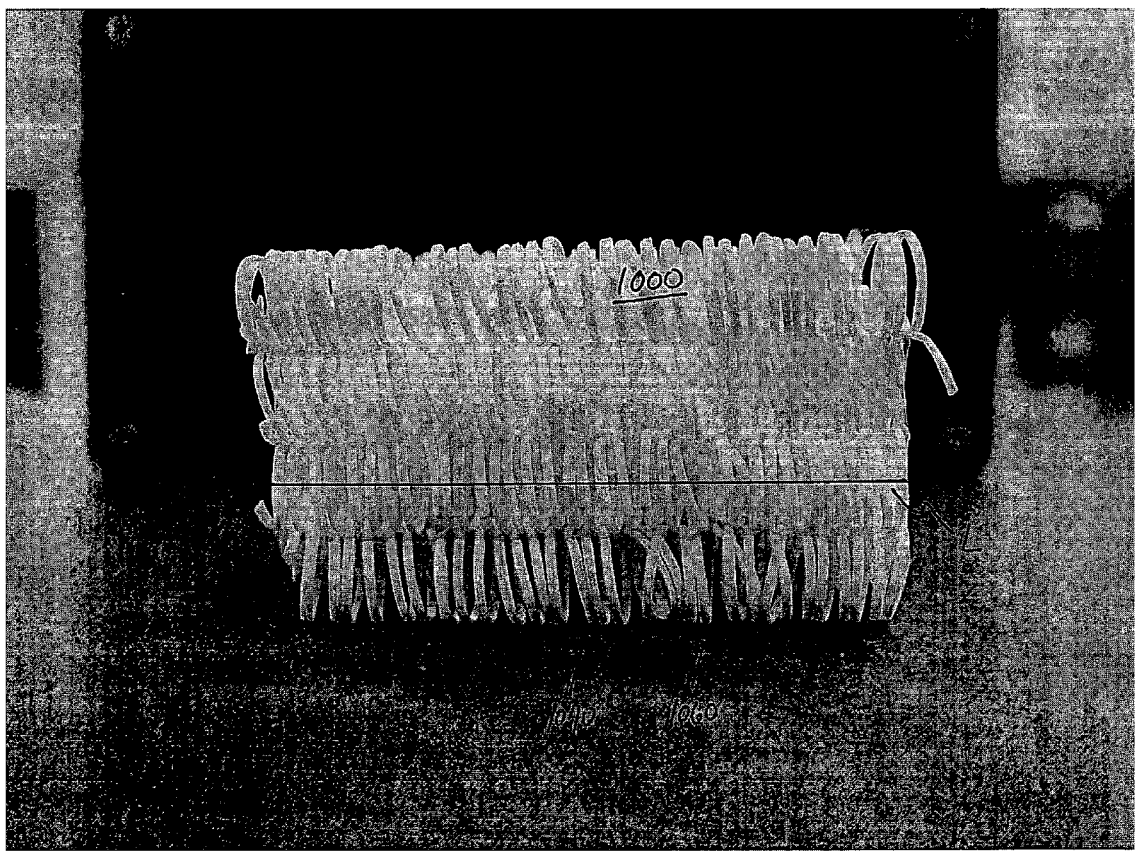
FIG. 12 is a picture illustrating a side view of the exemplary embodiment of FIG. 10.
Figure 13:
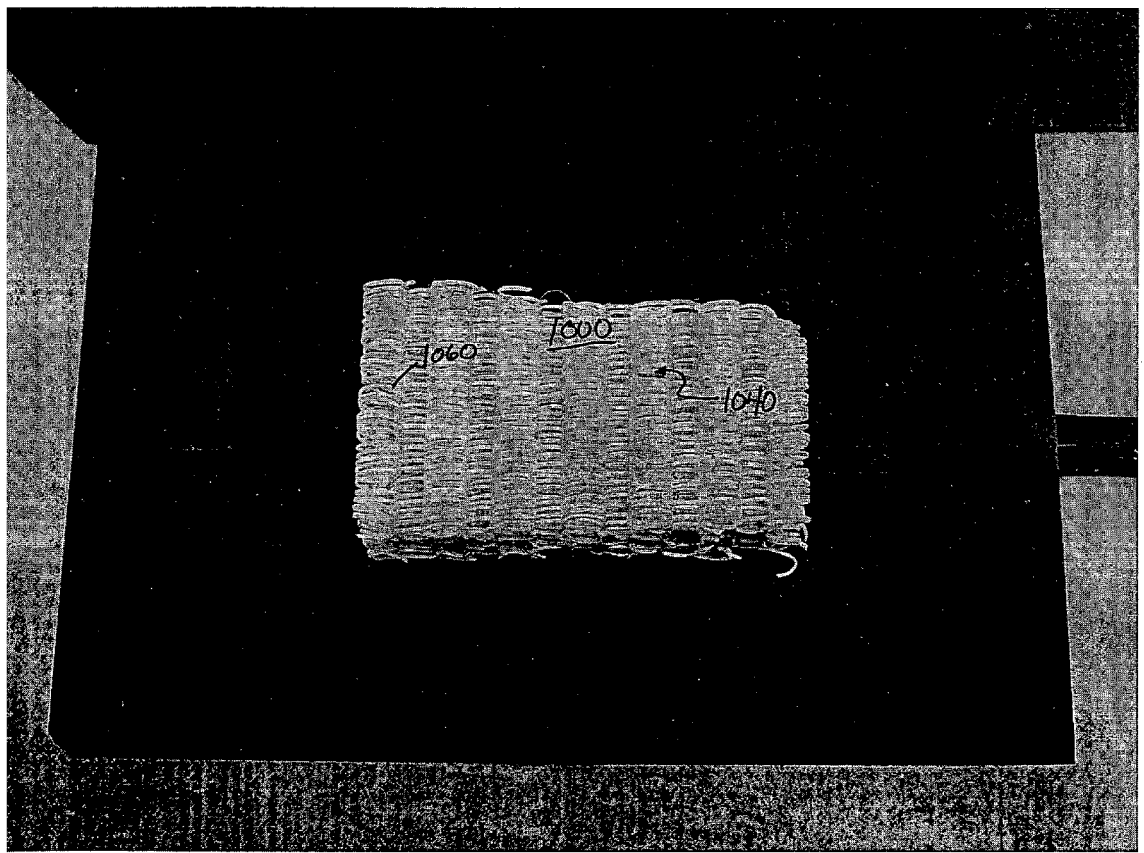
FIG. 13 is a picture illustrating a top view of the exemplary embodiment of FIG. 10.

FIG. 10 illustrates another exemplary embodiment of the present invention. As shown in FIG. 10, wound packing material 1000 has a generally spiral shape exhibiting open areas 1020 along the longitudinal axis of the fiber spiral and open areas 1040 between adjacent segments of a particular spiral. Wound packing material 1000 is generally constructed from polymer fibers 1060, such as spandex.

To form wound packing material 1000, fibers 1060 are wrapped around mandrels, such as a steel tube (not shown). The steel tubes with the spandex wrap are stacked in rows and a polyurethane film (not shown) is placed between each row. Desirably, the polyurethane film is about 0.003 inch thick. The stack of tubes is then clamped together and heated to about 320 degrees F. The polyurethane film melts and adheres to the spandex fibers, thus coupling the adjacent spirals to one another. After cooling, the steel tubes are removed. Wound packing material 1000, as illustrated in FIGS. 10-13 remains.

Wound packing 1000 benefits from a number of valuable properties. It is generally nonabsorbent, it is compressible and resilient such that it rebounds after compression and can be configured in an anisotropic fashion.

Additional embodiments are anticipated. A suitable wound packing can be made by spraying molten filaments on a conveyor with a waffled surface. A biocompatible binding agent is sprayed onto a three dimensional form, subsequently a chopper gun is used to spray chopped fibers with the desired properties onto the form. The binding agent serves to couple the fibers together forming an appropriate wound packing.

While preferred embodiments of the invention have been shown and described herein, it will be understood that such embodiments are provided by way of example only. Numerous variations, changes and substitutions will occur to those skilled in the art without departing from the spirit of the invention. Accordingly, it is intended that the appended claims cover all such variations as fall within the spirit and scope of the invention.

What is claimed:

1. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis, the second compressive response being different from the first compressive response, said nonabsorbent anisotropic structure comprising at least two layers, each layer being formed from biocompatible fibers coupled together, each layer being coupled to another layer, said at least two layers comprising a substantially flat first layer having an upper surface and a lower surface and a second layer having a nonlinear cross section with a plurality of peaks and troughs, wherein said troughs of said second layer are coupled to said upper surface of said first layer to form a corrugated unit and wherein said corrugated unit is interconnected to another corrugated unit by coupling said peaks of said second layer of one corrugated unit to the lower surface of said first layer of an adjacent corrugated unit.

2. The wound packing of claim 1, wherein said peaks of at least one corrugated unit are aligned with said peaks of an adjacent corrugated unit.

3. The wound packing of claim 1, wherein said peaks of at least one corrugated unit are staggered with respect to said peaks of an adjacent corrugated unit.

4. The wound packing of claim 1, wherein said corrugated unit is sliced along a cross-section perpendicular to said layers.

5. The wound packing of claim 1, wherein said corrugated units are sliced along a cross-section at a bias with respect to said layers.

6. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis, the second compressive response being different from the first compressive response, said nonabsorbent anisotropic structure comprising at least two layers, each layer being formed from biocompatible fibers coupled together, each layer being coupled to another layer, said at least two layers comprising a substantially flat first layer having an upper surface and a lower surface and a second layer having a nonlinear cross section with a plurality of peaks and troughs, wherein said troughs of said second layer are coupled to said upper surface of said first layer to form a corrugated unit and wherein said second layer comprises one or more beads of silicone disposed in a direction perpendicular to said peaks and troughs.

7. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis the second compressive response being different from the first compressive response and wherein said wound packing further comprises a second fiber comprised of a healing agent.

8. The wound packing of claim 7 wherein said second fiber comprises a calcium alginate fiber.

9. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis, the second compressive response being different from the first compressive response and wherein said fibers comprise a wound healing agent.

10. The wound packing of claim 9 wherein said wound healing agent is one of antimicrobial silver and hyaluronic acid.

11. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis, the second compressive response being different from the first compressive response and wherein said wound packing further comprises a second fiber adapted to conduct an electric current to at least one surface of the wound.

12. A wound packing for application to a wound under a cover, the cover establishing a confined space in which said wound packing is located and to which suction is applied to remove wound exudates from the wound and from said wound packing while said wound packing is in place, said wound packing promoting wound contraction along an axis, said wound packing being arranged for facilitating the transfer of wound exudates from the wound and from said wound packing, said wound packing comprising a plurality of biocompatible nonabsorbent fibers coupled together to form a nonabsorbent anisotropic structure having a first compressive response along a first axis and a second compressive response along a second axis perpendicular to the first axis, the second compressive response being different from the first compressive response, and wherein said fibers are adapted to conduct an electrical current to at least one surface of the wound.

* * * * *